(12) United States Patent
Ohlsson

(10) Patent No.: US 6,488,530 B2
(45) Date of Patent: Dec. 3, 2002

(54) INTERFACE UNIT FOR AN ELECTROPHYSIOLOGICAL MONITORING SYSTEM

(75) Inventor: Thomas Ohlsson, Hässelby (SE)

(73) Assignee: Siemens Aktiengesellschaft, Munich (DE)

(*) Notice: Subject to any disclaimer, the term of this patent is extended or adjusted under 35 U.S.C. 154(b) by 43 days.

(21) Appl. No.: 09/801,545

(22) Filed: Mar. 7, 2001

(65) Prior Publication Data
US 2001/0021799 A1 Sep. 13, 2001

(30) Foreign Application Priority Data
Mar. 9, 2000 (SE) ................................................ 0000778

(51) Int. Cl.[7] ................................................. H01R 3/00
(52) U.S. Cl. ...................................................... 439/491
(58) Field of Search ........................ 439/491, 49, 490, 439/489, 536; 434/72, 382; 235/375, 385

(56) References Cited

U.S. PATENT DOCUMENTS

| | | | |
|---|---|---|---|
| 5,265,607 A | | 11/1993 | Moberg |
| 5,487,666 A | * | 1/1996 | DiGiovanni ................ 439/491 |
| 5,735,708 A | * | 4/1998 | Arnett et al. ............... 439/491 |
| 5,821,510 A | * | 10/1998 | Cohen et al. ............... 235/375 |
| 6,234,830 B1 | * | 6/2001 | Ensz et al. .................. 439/491 |

* cited by examiner

Primary Examiner—Neil Abrams
Assistant Examiner—J. F. Duverne
(74) Attorney, Agent, or Firm—Schiff Hardin & Waite

(57) ABSTRACT

An interface unit for establishing an electrical coupling of a number of sensor wires from a combination of catheters with a number of electrical signal channels of a electrophysiological monitoring system has a number of electrical contacts for coupling individual wires with individual channels. Each contact is releasably engageable with an individual wire. A number of overlays which are removably locatable at the outer surface and are attached to the housing of the unit by binding rings. Each overlay carries on a face thereof a visible indication of a different one of a number of stored wire/contact configurations. The configurations are organized such that contacts for receiving wires from a same catheter are grouped together and the indication is formed as visibly differentiated regions, each de-marking a different grouping.

12 Claims, 5 Drawing Sheets

INTERFACE UNIT FOR AN ELECTROPHYSIOLOGICAL MONITORING SYSTEM

BACKGROUND OF THE INVENTION

1. Field of the Invention

The present invention relates to an interface unit for an electrophysiological measurement system of the type which allows electrical connections to be established between wires from catheter-mounted electrodes and a monitoring system in a variable manner, and in particular to a unit which includes a display for displaying a connection configuration.

2. Description of the Prior Art

Electrophysiological measurement systems generally include a monitoring system for one or more of receiving, storing, processing and displaying signals from a number of patient interactive elements such as catheter-mounted intracardiac electrodes, surface ECG electrodes, blood parameter sensors, and other physiological parameter sensors, and an interface unit. The monitoring system often includes a switching unit by which measurements may be selectively made using different combinations intracardiac electrodes.

The interface unit is typically disposed bedside to receive the proximal ends of wires which are connected at their distal ends to the patient interactive elements and to provide for their electrical connection to the switching unit of the monitoring system. The wires are received by the interface unit in releasable engagement with input terminals which, for the intracardiac electrodes, are often arranged at the outer surface of the unit in a grid fashion. An output socket is provided for electrical connection to the switching unit and has contacts, each of which is in fixed connection with a corresponding input terminal. Which electrode wire connects to which terminal is dependent largely on the combination of catheters being used for a particular physiological examination, the nature of that examination and how the monitoring system is configured to receive the electrical signals.

Before undertaking any physiological examination the system must be set-up so that the correct catheter wires are connected with the correct terminals on the interface unit. To facilitate this set-up it is known to provide an interface unit wherein each terminal is permanently labeled in numerical sequence for identification purposes. Each wire of a particular catheter is usually provided with an identifying label by the manufacturer. Look-up tables can be constructed using these two sets of labels to indicate the wire/terminal configuration required for a particular study. A wipe-clean surface may be available on the interface unit so that a non-permanent label can be provided for each terminal used in the examination which identifies the catheter electrode wire to be inserted according to the look-up table. Often during a physiology study, however, it is desirable either to move a catheter to a different measurement location, to alter the combination of catheters, or to re-define the measurement protocol for the same catheter combination. In any of these events, it is necessary to reconfigure the interface unit connections and in the process replace the particular labels on the interface unit to correspond with the new configuration. This can be tedious and time-consuming for the operator and may lead to an incorrect configuration being made during the two step process of identifying the correct look-up table and then transferring the tabulated assignments to visible labels on the interface unit.

To alleviate this problem it is known from U.S. Pat. No. 5,640,967 to provide an "intelligent" device which combines switching, amplification and interface functions in a single, compact bedside unit. A microprocessor controlled LCD screen display is provided to graphically display the connection configuration required for a particular measurement protocol. A memory also is provided for storing a library of different configurations for later retrieval and display.

With the additional electronic components this is relatively expensive to implement compared with the existing "dumb" interface unit in which essentially only the releasable connections between wires and terminals are selectively established (the connection between each terminal and a corresponding output pin of the unit remains fixed). Moreover, the use of an LCD display does not itself address the problem of the construction of readily interpretable labels.

An additional problem can result from the manufacturer's normal practice of labeling the wires connecting each electrode of a particular catheter in numerical order, when trying to establish the correct electrode wire connection at the interface unit, since each catheter in a combination of catheters will contain identically identified wires. Labels in this circumstance cannot be easily constructed which provide for an intuitive (and thus inherently safer) correlation between wire and terminal.

SUMMARY OF THE INVENTION

An object of the present invention is to provide an interface unit wherein a library of wire/contact configurations can be established relatively inexpensively and without the addition of complex electronic components, thereby providing a unit in which the visual portrayal of wire/catheter combinations can be readily varied.

The above object is achieved in accordance with the principles of the present invention in an interface unit for an electrophysiological monitoring system having a plurality of electrical receptacles for respectively receiving individual wires for different channels of the monitoring system, each receptacle being releasably engageable with the individual wire, and a display at an exterior surface of the interface unit which provides a visual indication of a wire/receptacle configuration for each of the number of stored configurations. In one embodiment, the display is formed by a number of overlays which are individually and removably placeable at the exterior surface. Each overlay, on an overlay face thereof, carries a visible indication of a different one of the stored configurations.

In another embodiment, the receptacles are disposed in a grid on the exterior surface of the interface unit in different groups, and the display is permanently disposed at the exterior surface and provides a visual indication of each grouping of the receptacles.

Each overlay of the library may be retained on, and possibly movable over, binding posts which are attached to the housing of the interface unit. This arrangement helps maintain the integrity of the library and can aid the correlation of the overlay with the upper surface of the housing.

Preferably each overlay is constructed so that contacts for each catheter of a catheter combination are grouped together with the visible indication preferably including a visible demarcation, such as a lined or colored/shaded block demarcation or an interconnecting line demarcation, of the different groups of contacts; an identifier to visibly link an individual catheter to a particular contact grouping, for example a label or colour code identifier; and wire label identifiers which preferably correspond to the catheter manufacturer provided wire identifiers. In this manner a readily interpretable indication of the expected wire/contact configuration is provide in a single overlay without having to memorize or frequently record complex and abstract "artificial" label identifiers. This grouping and labeling arrangement also can be employed to similar advantage with other display types such as an LCD screen display or a permanently fixed display.

DESCRIPTION OF THE PREFERRED EMBODIMENTS

Figure 1:
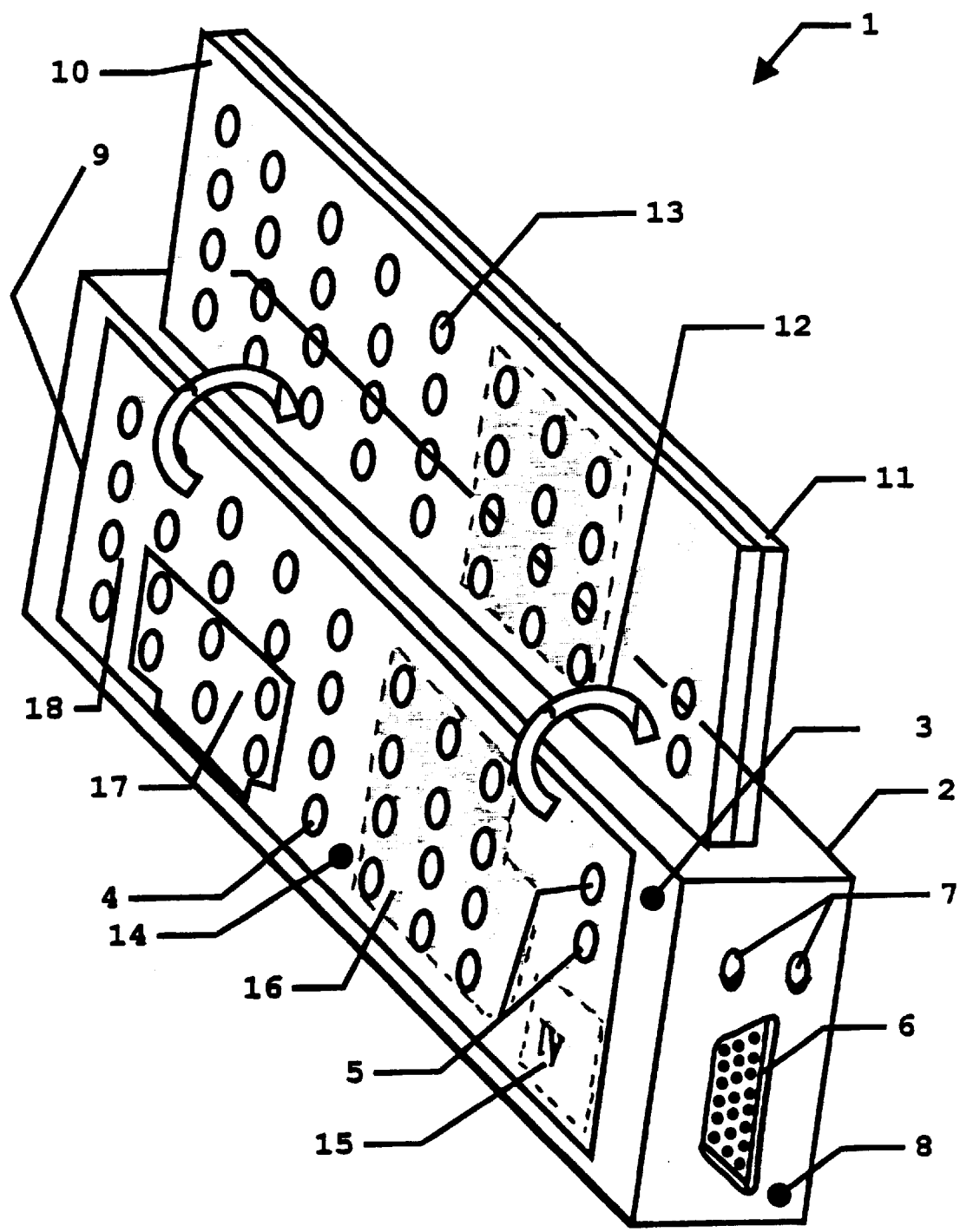
FIG. 1 is a perspective view of an interface unit according to the present invention.

The interface unit 1 of FIG. 1 has a housing 2 with an outer surface 3 on which a number of jacks or sockets (shown generally at 4) are arranged in a grid, for example thirty two jacks arranged in a four-by-eight matrix are illustrated, and two further jacks 5. These jacks 4,5 provide for a releasable engagement with complementary jack plugs of intracardiac catheter electrode wires (not shown). A standard "D-connector" 6 and two jacks 7 are provided in a side-wall 8 of the housing 2 and are made in hard-wired connection within the housing 2 respectively to the grid arranged jacks 4 and the two other jack 5 within the housing 2. Alternatively, the D-connector 6 may be provided with connections to the two further jacks 5, and the jacks 7 in the side-wall 8 omitted. Moreover, the D-connector 6 maybe replaced by a multi-core wire which is permanently connected to the jacks 4,5.

A number of overlays 9–11 are also releasably connected to the housing 2 by means of ring-binders 12 and are provided with a number of holes (shown generally at 13) which, when an overlay 9 is correctly located on the surface 3, correspond with the jacks 4,5 to permit their electrical connection with catheter wires. Each overlay 9–11 can be moved on or removed from the ring-binders 12 between a position (overlays 10–11) away from the outer surface 3 and a position (overlay 9) on the surface 3 in which it overlays the jacks 4,5. Each overlay 9–11 has on an upper face 14 (when positioned on the outer surface 3 of the housing 2), a visible indication of different wire/jack 4 inter-connections necessary to allow a particular electrophysiological examination to be undertaken using a particular catheter combination, as will be described more fully below in relation to FIG. 3. Each overlay 9–11 may be provided with an identification label 15 (see FIGS. 2, 2a and 2b) by which a user can confirm that the correct overlay 9–11 is placed uppermost on the surface 3 of the housing 2.

Figure 2A:
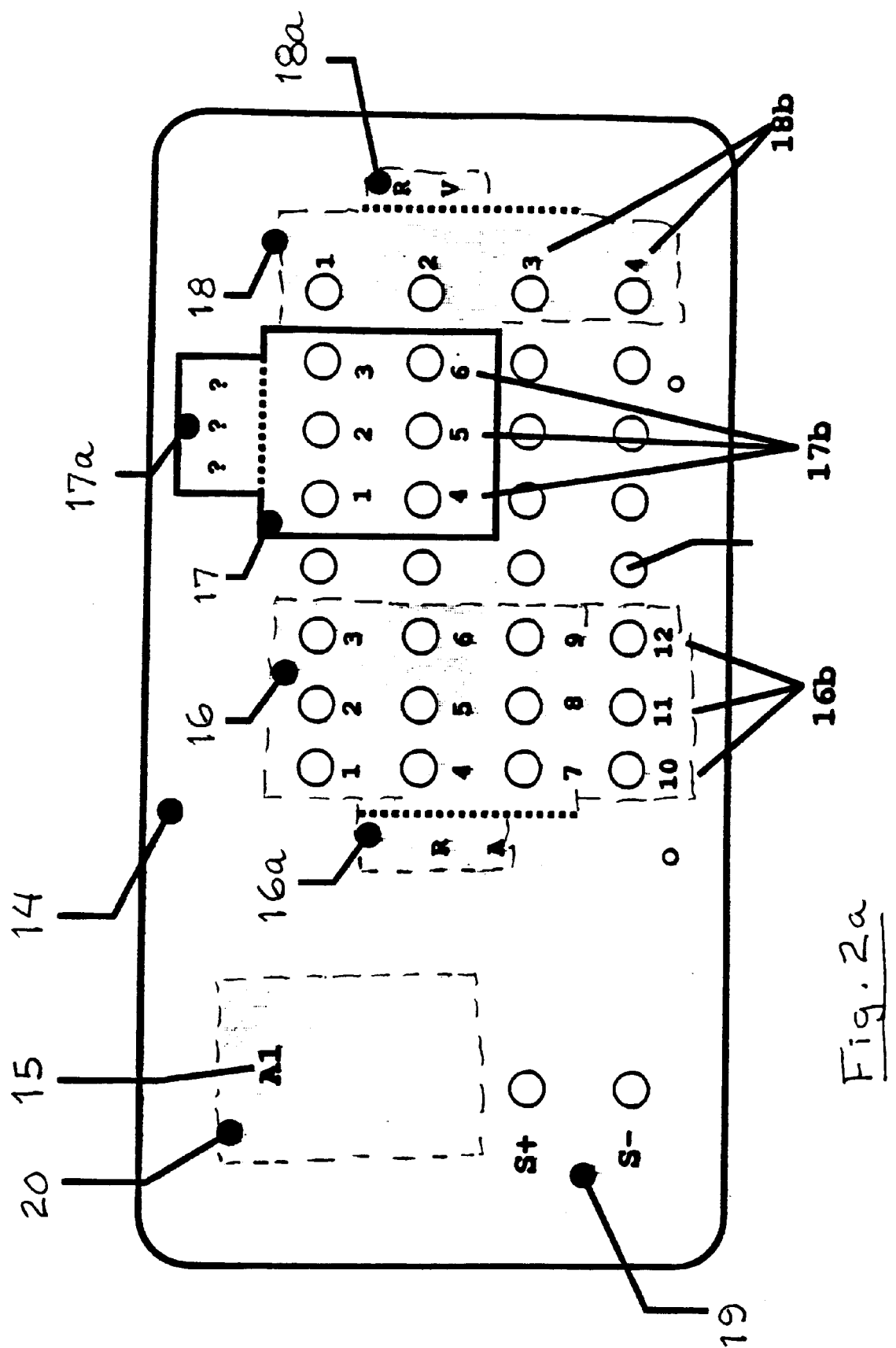
FIGS. 2a and 2b show representations of overlay cards for use with an interface unit according to the present invention.

In FIG. 2a an example of an overlay 9 usable with the interface unit 1 of FIG. 1 is illustrated. The overlay 9 is a thin, flexible sheet of, for example, acetate or other plastic, through which a number of holes 13 have been made, each one disposed so that it allows access to a corresponding one of the jacks 4,5 when the overlay 9 is located on the outer surface 3 of the housing 2. On one face 14 of the sheet a visible indication is provided to guide the inter-connection of wire and jack 4 for a particular combination of catheters (here three catheters, one with twelve wires, one with six and one with four).

This indication may be formed by one or both opaque blocks 16,18, (since an opaque block cannot be shown in the drawings, the boundaries of the opaque blocks are indicated with dashed lines which, it will be understood, are not actually present on the face 14) and boundary demarcation line 17 arranged on the face 14 to provide a visible demarcation between jacks for different catheters. Each indication 16,17,18 has a catheter label area 16a, 17a, 18a on which a catheter identifier is provided. The identifier may, for example, be selected from the well known "RA", "RV" etc. notations which clinicians use to indicate locations within the heart and so provides an intuitive indication of which catheter to connect.

Each indication 16,17,18 also has wire label areas (shown generally at 16b, 17b, 18b but not necessarily having visible boundaries)on which wire identifiers, for example numerals "1,2,3 . . ." corresponding to the manufacturer-provided designations, are provided, each in registration with an individual hole 13. An indication block 19 also is provided which delimits the non-grid jacks 5 which are provided specifically to accept jack plugs from stimulation electrodes and are labeled "S+" and "S−" (identifying the polarity of the stimulation pulse). Each overlay is provided in the block 20 with the unique identifying label 15, such as an alphanumeric "A1". Thus, as can be appreciated from the illustration of the overlay 9 presented in FIG. 2a, this arrangement provides a visible indication by which catheter leads from different catheter combinations can be readily and intuitively linked with the correct jack 4, since the grouping of jacks for each catheter is clearly shown by the indications 16,17,18 and since for each catheter, the wire labels 16b, 17b, 18b preferably correspond to the labels placed on individual wires by the manufacturer.

Figure 2B:
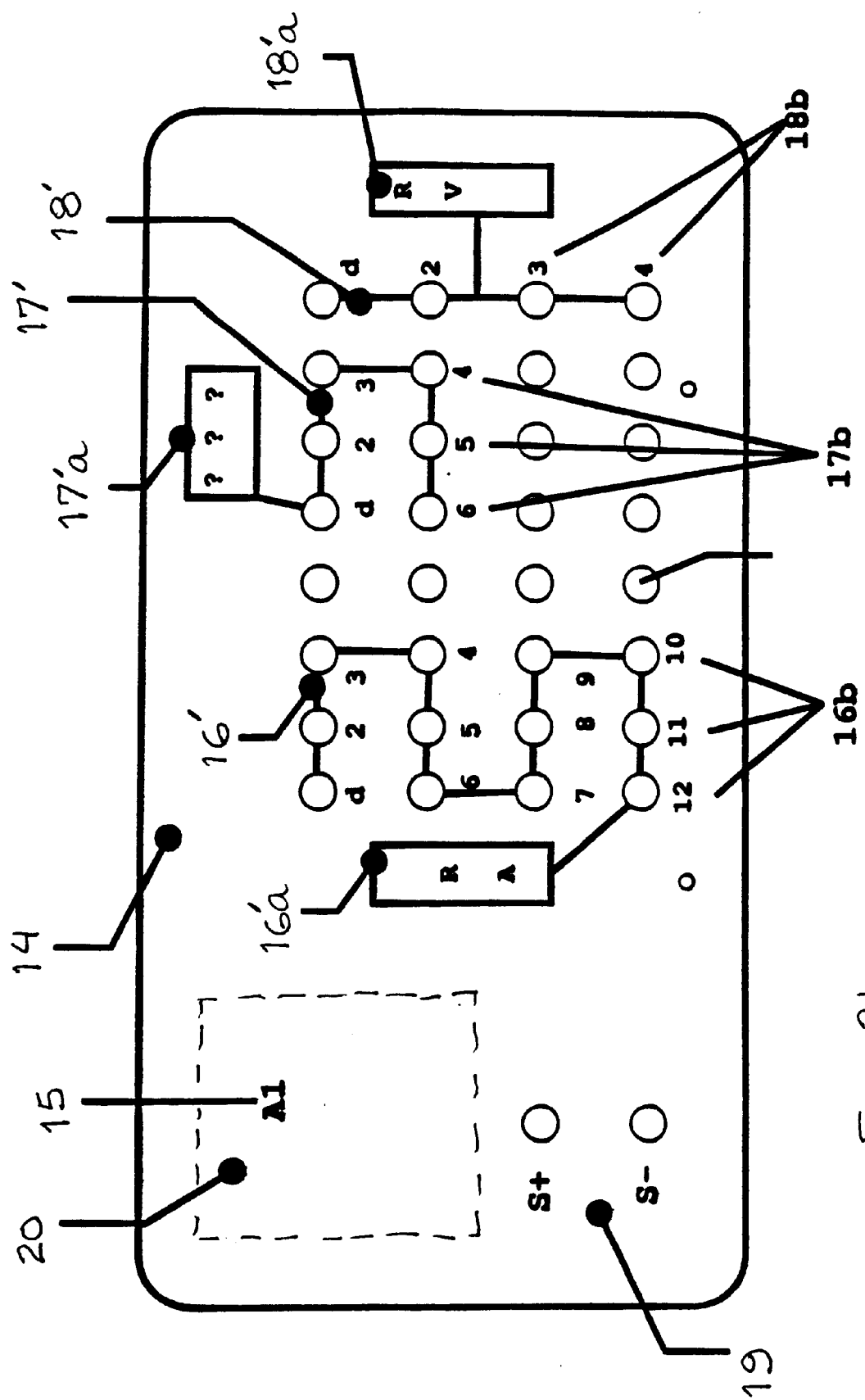

An alternative overlay 9 is shown in FIG. 2b in which indication blocks 16,17,18 are replaced by a corresponding inter-connecting line 16', 17', 18'. Each line 16', 17' 18' is arranged to inter-connect a different combination of the holes 13 in order to differentiate the individual catheter contact groupings. The catheter label areas 16'a, 17'a and 18'a, which correspond to the label areas 16a, 17a, 18a of the overlay 9 of FIG. 2a are shown linked to their respective lines 16', 17', 18' by a connecting line. The overlay identifier label 15 is again placed within the block.

These unique and inventive visible indications, here shown on the surfaces 14 of the removable overlays 9 of FIGS. 2a and 2b, may be provided as a permanently fixed display marked on the surface of a housing 2 similar to the interface unit 1 of FIG. 1, or can be displayed using an integral, preferably flat panel, display screen (not shown).

Figure 3:
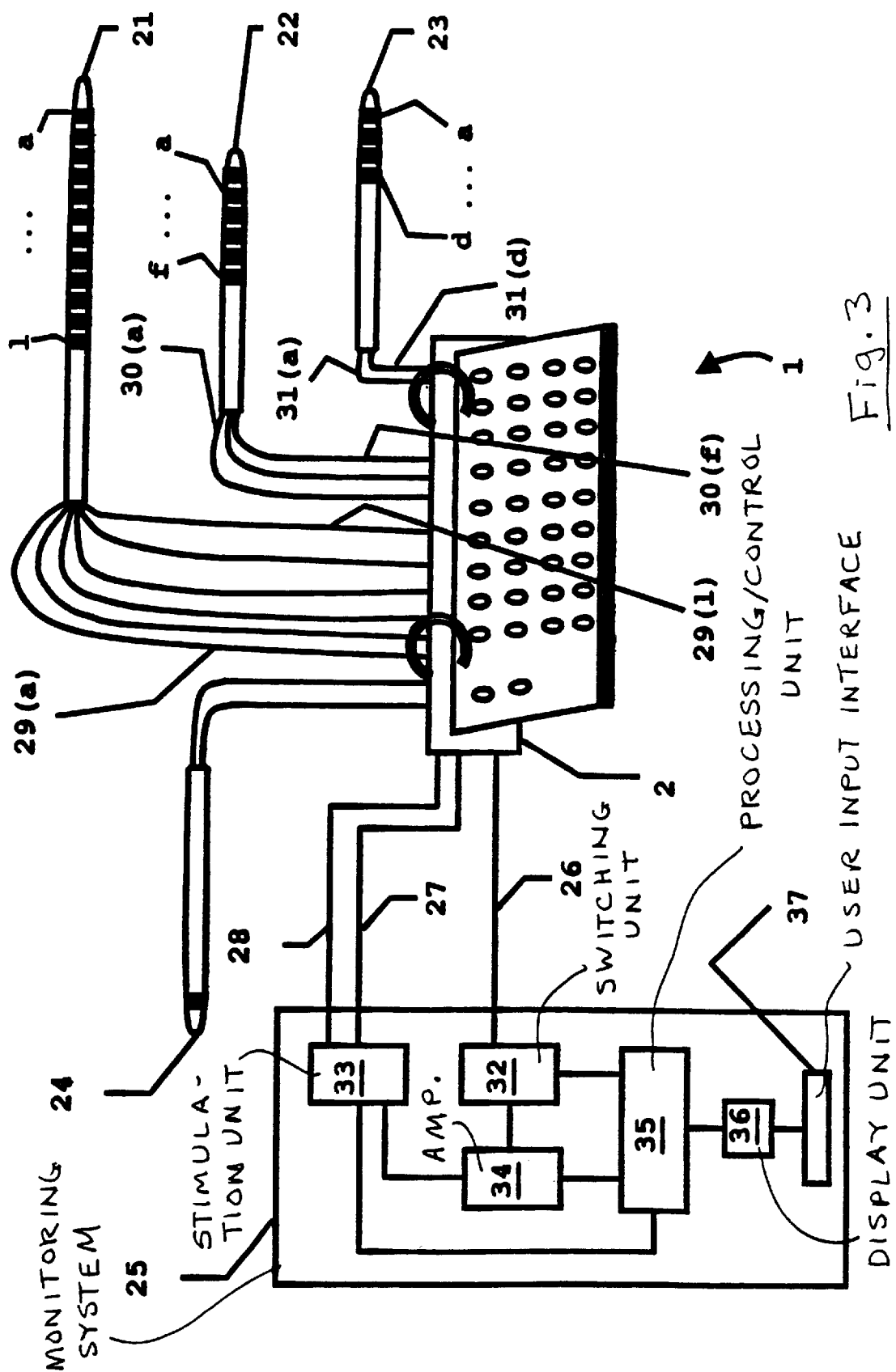
FIG. 3 is a schematic diagram illustrating the components of a electrophysiological measuring system having an interface unit according to the present invention.

The selection and construction of these overlays 9–11 may be better understood from a description of the operation of the electrophysiological measurement system of FIG. 3, in which three intracardiac measurement catheters 21,22,23 and one intracardiac stimulation catheter 24 are shown in electrical connection to jacks 4,5 (FIG. 1) in the housing 2 of the interface unit 1. An electrophysiological monitoring system 25 is electrically connected to the jacks 4,5 via the D-connection 6 (FIG. 1) and the input jacks 7 (FIG. 1) by respective wires 26 and 27,28. A number of measurement electrodes 21a–l; 22a–f and 23a–d are located on the respective catheters 21,22,23 for insertion into the heartland are connected to a corresponding number of wires 29a–l; 30a–f; 31a–d. These wires 29a–l; 30a–f; 31a–d are provided at their free ends with jack plugs (not shown) for releasable connection with the jacks 4 (FIG. 1) of the interface unit 1 and are labeled in numerical sequence starting at one (or sometimes "d" as shown in FIG. 2b) for each of the catheters 21–23.

The monitoring system 25 includes a switching unit 32, a stimulation unit 33, an amplifier unit 34, a processing/control unit 35, a display monitor 36 and a user input interface 37. It will be appreciated by those skilled in the art that these units are typically found in known electrophysiological monitoring systems where other components may also be found, such as a printer, a remote communications unit and the like, and which are not intended to be excluded from the system 25 of the present example. For ease of reference and understanding, each unit 32–37 is illustrated as being a separate item, but it is well-known that the functionality of some or all of the individual units may be provided in a single physical unit such as a suitably configured and programmed personal computer or a dedicated microprocessor unit.

The wire 26 provides electrical connections between the individual jacks 4 of the interface unit 1 and individual input channels of the switching unit 32. The unit 32 has electrically actuated switches (not show) which can be opened and closed in an optional manner by control signals supplied from the processing/control unit 35, so as to allow for electrophysiological measurements to be made within the processing/control unit 25, using selected combinations of electrodes of the connected catheters 21–23. Thus it can be seen that for a. particular arrangement of open and closed switches the measurements made will depend on the wire/jack configuration at the interface unit 1.

The processing/control unit 35 also includes a storage device, such as a computer hard disc, on which several predefined switch arrangements are stored, each linked with a different one or more expected wire/jack configurations, and an indication of the electrophysiological measurements performed by a particular configuration/arrangement combination. This information may be stored by the manufacturer of the equipment and additionally or alternatively may be added by a user during a system set-up procedure outlined below.

For each different wire/jack configuration an overlay card 9–11 (FIG. 1) is provided at the interface unit 1 with a visible indication of the particular configuration, as described above in relation to FIG. 1 and FIGS. 2a and 2b, on a face 14. The monitoring system 25 is configured to operate so the user may indicate on the display monitor 36, using the user input interface 37, such as an alpha-numeric keyboard or mouse, a particular electrophysiological study and a particular catheter combination (of course if one or other of these parameters is fixed then only the variable one need by indicated). The processing/control unit 35 processes the choice and selects the overlay 9–11 which provides the particular wire/jack combination needed to fulfil the choice. A visible indication of the particular overlay 9–11 (FIG. 1) which provides this combination is generated on the display screen 36 by the unit 35. This indication may be the identifier label 15 (FIGS. 2a and 2b) of an overlay 9 or could additionally or alternatively be a graphical image depicting the upper surface 14 of the necessary overlay. The overlays 9–11 on the ring binders 13 are flipped through and the correct overlay is placed uppermost on the surface 3 of the interface unit housing 2 (FIG. 1). Catheter wires 29(a–l), 30(a–f), 31(a–d) are then inserted according to the indications on the overlay surface 14.

If the electrophysiological examination or the particular catheter combination is new, then a set-up routine within the processing/control unit 35 enables a user to define the switch arrangement to be employed in the switching unit 32 and also the catheter wire/interface unit contact arrangement, if this is new. The processing/control unit 35 then adds the new switch arrangement to the store of existing arrangements with a link to a different one or more expected wire/jack configurations and with an indication of the electrophysiological measurements performed by a particular configuration/arrangement combination.

Figure 4:
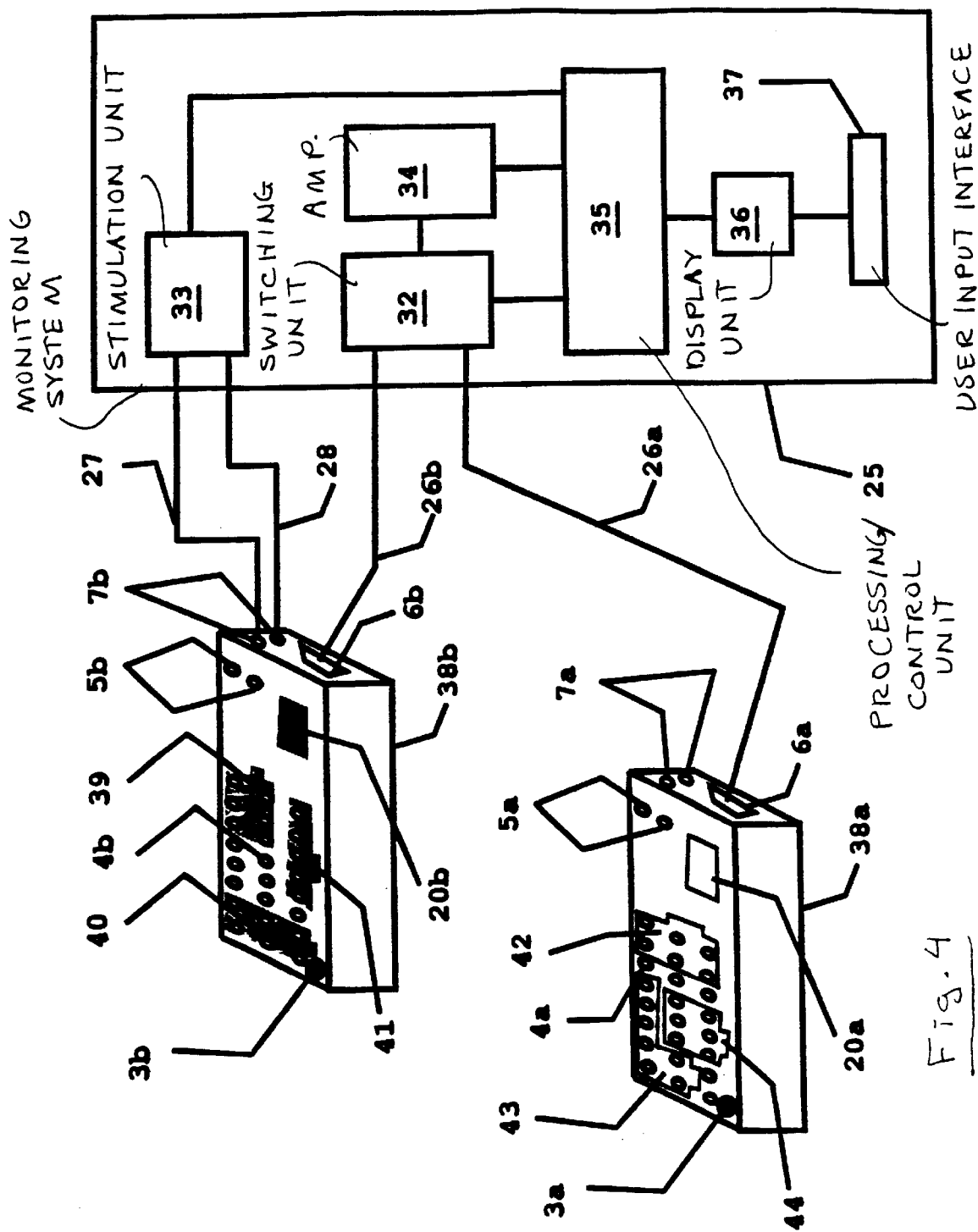
FIG. 4 is a schematic diagram illustrating an alternative electrophysiological measuring system in accordance with the invention.

When defining a new wire/contact arrangement the user may be presented with an image on the display screen 36 illustrating a blank overlay and prompted to input, using the user input interface 37, the number of catheters and their number of wires (optionally with the manufacturer's own wire identification labels). The processing/control unit 35 can be programmed to calculate and display a suitable catheter arrangement on the blank overlay in which the wires for each catheter are grouped together and in which a visible demarcation is provided on a new overlay to indicate the separate catheter groupings. Alternatively, the user may be permitted to form these groupings manually on the screen image of the overlay. When the groupings have been formed the user provides identifying labels as well as wire indicators, which in default are a number sequence typically used by catheter manufacturers as wire identifiers. These identifying labels and wire indicators are presented on the screen image in regions corresponding to catheter label areas 16a, 17a, 18a; 16'a, 17'a, 18'a and wire label areas 16b, 17b, 18b; 16'b, 17'b, 18'b on the actual overlay 9 (FIG. 2). The user indicates acceptance of the overlay layout presented on the screen 36 using the interface 37 and provides a unique overlay identifying label 15 which is entered on the screen image in the region corresponding to the identifier block 20 (FIG. 2) on the actual overlay 9. Alternatively, this label 15 may be generated by the processing/control unit 35. The processing/control unit 35 then processes this screen image to provide printer control commands for use by an optional printer (not shown), such as a conventional ink-jet or laser printer, which prints the image on a blank overlay sheet that, for convenience may be pre-formed with the through-holes 13 (FIG. 2). FIG. 4 shows an alternative electrophysiological measurement system in which elements corresponding to elements shown in the system of FIG. 3 and the interface unit of FIG. 1 are given corresponding reference numerals. A switch unit 32 of a monitoring system 25 is connected via signal cables 26a, 26b to two interface units 38a, 38b, each of which unit is intended to interface with a different combination of catheters necessary to carry out an electrophysiological study. Each interface unit 38a, 38b is similar in configuration to the interface unit of FIG. 1 and comprises a number, shown here as twenty four, input jacks 4a,4b arranged in a grid, here a eight-by-three matrix, on an outer surface 3a, 3b. Dedicated stimulation catheter jacks 5a,5b are also provided in this surface 3a,3b and all jacks 4,5 are hard wired respectively to D-connectors 6a,6b and to further jacks 7a,7b. These further jacks 7a,7b are available for releasable connection with input wires 27,28 of a stimulator unit 33 which is controlled by a processing/control unit 35 to provide electrical signals useable to stimulate activity in a heart during an examination.

Each interface unit 38a,38b has formed on the surface 3a,3b containing the jacks 4a,4b a permanent visible indication of the wire/contact configuration for a particular combination of catheters (here illustrated as three for each unit). This indication is essentially that described above for the overlay of FIGS. 2a and 2b and includes a visible demarcation between groupings of jacks 4 for the different catheters. This demarcation may be, for example, in the form of colored or shaded regions 39,40,41 or simply line markings 42,43,44 around the periphery of each grouping. Also provided on the surfaces 3a, 3b are labels 20a, 20b which may be used to identify the particular interface box 38a, 38b to the user and to the monitoring system 25.

The above embodiments of the interface unit according to the present invention have been described in relation to intracardiac catheter electrodes, but it will be appreciated by those skilled in the art that the interface unit may be modified to additionally receive input wires from other patient interactive elements (ECG wires, pressure sensors and blood gas sensors, for example) and may be provided with a different number of contacts within the grid arrangement without departing from the scope of the invention as claimed.

I claim as my invention:

1. An interface unit for an electrophysiological monitoring system, said interface unit having an exterior surface and comprising:

a plurality of electrical receptacles each adapted to receive a different one of a plurality of individual wires for respectively uniquely coupling the individual wires with different electrical channels, each of said receptacles being adapted to releasably engage an individual wire;

a display placeable at said exterior surface for providing a visual indication of a wire/receptacle configuration from among a plurality of stored wire/receptacle configurations, said display comprising a plurality of overlays, each being removably placeable at said exterior surface, and each of said overlays having an overlay face carrying a visible indication of a different one of said plurality of stored wire/receptacle configurations.

2. An interface unit as claimed in claim 1 wherein each of said overlays has a plurality of openings therein and wherein said visible indication comprises a plurality of labels respectively identifying individual wires in said one of said stored configurations, said labels being disposed to respectively identify said openings for said individual wires.

3. An interface unit as claimed in claim 2 wherein said receptacles are disposed on said exterior surface and wherein said openings in each overlay are in registration with the receptacles for said one of said configurations for which the overlay provides said visible indication.

4. An interface unit as claimed in claim 1 comprising a plurality of binder rings for retaining said overlays relative to said exterior surface.

5. An interface unit as claimed in claim 4 wherein the overlays in said plurality of overlays are individually movable on said binding rings to place a selected one of said overlays uppermost at said exterior surface.

6. An interface unit as claimed in claim 1 wherein said receptacles are disposed in a grid at said exterior surface, and wherein the visible indication on at least one of said overlays identifies a grouping of said receptacles within said grid.

7. An interface unit as claimed in claim 6 wherein said visible indication for said grouping is a color-differentiated region of said overlay.

8. An interface unit as claimed in claim 6 wherein said visible indication of said grouping is a boundary line demarcation.

9. An interface unit for an electrophysiological monitoring system, said interface unit having an exterior surface and comprising:

a plurality of electrical receptacles arranged in a grid at said exterior surface, each of said receptacles being adapted to releasably receive a different one of a plurality of individual wires to uniquely electrically connect the individual wire received therein with an electrical channel, said wires proceeding from a plurality of individual catheters; and a display permanently disposed at said exterior surface and providing a visual indication of respective groupings of said receptacles in said grid corresponding to groups of wires proceeding from one of said catheters.

10. An interface unit as claimed in claim 9 wherein said display forms said exterior surface.

11. An interface unit as claimed in claim 10 wherein said visible indication is a color-differentiated region of said exterior surface.

12. An interface unit as claimed in claim 10 wherein said visible indication is a boundary line demarcation on said exterior surface.

* * * * *